United States Patent
Bhasin

(10) Patent No.: US 9,944,893 B2
(45) Date of Patent: Apr. 17, 2018

(54) METHOD FOR ORGANIC WASTE HYDROLYSIS AND ACIDIFICATION AND AN APPARATUS THEREOF

(71) Applicants: UTB ENVIROTEC ZRT., Budapest (HU); Charandeep Singh Bhasin, Budapest (HU)

(72) Inventor: Charandeep Singh Bhasin, Budapest (HU)

(73) Assignee: RENEW TECHNOLOGIES LTD, Horsham (GB)

( * ) Notice: Subject to any disclaimer, the term of this patent is extended or adjusted under 35 U.S.C. 154(b) by 168 days.

(21) Appl. No.: 14/440,880

(22) PCT Filed: Nov. 5, 2013

(86) PCT No.: PCT/HU2013/000105
§ 371 (c)(1),
(2) Date: May 6, 2015

(87) PCT Pub. No.: WO2014/072756
PCT Pub. Date: May 15, 2014

(65) Prior Publication Data
US 2015/0299635 A1 Oct. 22, 2015

(30) Foreign Application Priority Data
Nov. 6, 2012 (HU) .................................. 1200637

(51) Int. Cl.
*C12M 1/107* (2006.01)
*C12M 1/00* (2006.01)
(Continued)

(52) U.S. Cl.
CPC ............ *C12M 23/36* (2013.01); *C02F 3/006* (2013.01); *C02F 3/12* (2013.01); *C12M 27/02* (2013.01);
(Continued)

(58) Field of Classification Search
None
See application file for complete search history.

(56) References Cited

U.S. PATENT DOCUMENTS 4,510,243 A 4/1985 Haga et al.
4,636,467 A * 1/1987 Chynoweth ............. C07C 53/10
435/136

(Continued)

FOREIGN PATENT DOCUMENTS

DE 102007017615 10/2008
DE 102009009985 8/2010
(Continued)

OTHER PUBLICATIONS

International Search Report for PCT Application No. PCT/HU2013/000105, dated Mar. 17, 2014.
(Continued)

*Primary Examiner* — Chris R Tate
*Assistant Examiner* — Douglas F White
(74) *Attorney, Agent, or Firm* — Pearl Cohen Zedek Latzer Baratz LLP

(57) ABSTRACT

The invention relates to a method and an apparatus for hydrolyzing and acidifying homogenized organic waste fed into a closed and gas tight reactor using enzymatic bacteria under thermophilic conditions where water may be added to said reactor and the content of the reactor can be mixed and subjecting during hydrolysis and acidification an adequate part of a suspension formed in the reactor to—i. a separation step isolating—a permeate comprising an aqueous solution of soluble carbon, volatile fatty acids (VFA) and valuable nutrients, —an organic slurry comprising an aqueous solution of insoluble organic solids rich in enzymatic thermophilic bacteria and non-hydrolyzed organic solids, and the remaining part of soluble carbon, VFA and valuable nutrients, thereafter to—ii. a recirculation step re-feeding said
(Continued)

organic slurry into the reactor for further hydrolysis and acidification.

5 Claims, 1 Drawing Sheet

(51) Int. Cl.
*C12M 1/34* (2006.01)
*C02F 3/00* (2006.01)
*C02F 3/12* (2006.01)
*C12M 1/06* (2006.01)

(52) U.S. Cl.
CPC ............ *C12M 29/00* (2013.01); *C12M 29/04* (2013.01); *C12M 29/18* (2013.01); *C12M 41/12* (2013.01); *C12M 41/26* (2013.01); *C12M 41/40* (2013.01); *C12M 45/06* (2013.01); *C02F 2203/006* (2013.01); *C02F 2209/02* (2013.01); *C02F 2209/06* (2013.01); *C02F 2209/225* (2013.01); *C02F 2301/106* (2013.01)

(56) References Cited

U.S. PATENT DOCUMENTS

| | | | |
|---|---|---|---|
| 4,659,471 A | 4/1987 | Molin et al. | |
| 5,237,865 A * | 8/1993 | Wada | B08B 9/0322 73/198 |
| 6,077,548 A * | 6/2000 | Lasseur | C12M 21/02 426/69 |
| 6,159,263 A | 12/2000 | Greer et al. | |
| 6,342,378 B1 * | 1/2002 | Zhang | C12M 21/04 210/203 |
| 6,966,983 B1 | 11/2005 | McWhirter et al. | |
| 7,927,491 B2 | 4/2011 | Kotelko et al. | |
| 2003/0158435 A1 * | 8/2003 | Joyce | C07C 41/16 560/24 |
| 2004/0115782 A1 | 6/2004 | Paterek et al. | |
| 2005/0035059 A1 * | 2/2005 | Zhang | B01D 61/04 210/605 |
| 2005/0252858 A1 | 11/2005 | Peyton et al. | |
| 2007/0122874 A1 * | 5/2007 | Suthanthararajan | C02F 3/286 435/41 |
| 2007/0158264 A1 * | 7/2007 | Zhang | C02F 3/286 210/603 |
| 2008/0187975 A1 * | 8/2008 | Kohn | C01B 3/501 435/167 |
| 2008/0311640 A1 * | 12/2008 | Cox | C12P 3/00 435/168 |
| 2010/0159539 A1 * | 6/2010 | Ascon | C12M 21/04 435/134 |
| 2010/0216201 A1 * | 8/2010 | Soong | C12P 7/06 435/161 |

FOREIGN PATENT DOCUMENTS

| | | |
|---|---|---|
| DE | 202009017017 | 2/2011 |
| DE | 19937876 | 3/2011 |
| EP | 0053777 | 11/1981 |
| EP | 2136938 | 12/2009 |
| JP | 2005-313120 | 11/2005 |
| WO | WO 00/39036 | 7/2000 |
| WO | WO 2010/085893 | 8/2010 |
| WO | WO 2011/010275 | 1/2011 |

OTHER PUBLICATIONS

Hungarian Search Report for Hungarian Application No. P1200637, dated Feb. 24, 2014.

* cited by examiner

001
METHOD FOR ORGANIC WASTE HYDROLYSIS AND ACIDIFICATION AND AN APPARATUS THEREOF

CROSS-REFERENCE TO RELATED APPLICATIONS

This application is a National Phase Application of PCT International Application No. PCT/HU2013/000105, International Filing Date Nov. 5, 2013, claiming priority of Hungarian Patent Application No. P1200637, filed Nov. 6, 2012, which are both hereby incorporated by reference.

The present invention relates to a method for hydrolyzing and acidifying homogenized organic solids contained in wastewater sludge, food processing waste (animal, fruit and vegetable, diary, etc.), commercial waste (grease, expired food), agricultural waste, organic municipal solid waste, animal manure, and industrial by-products like Category 2 and Category 3 waste (EU regulation No 1069/2009), or in a mixture thereof, in a closed and gas tight biological reactor under controlled conditions and to an apparatus thereof.

More particularly, the present invention includes a step of subjecting organic solids to enzymatic hydrolysis and acidification to separate valuable components and reclaim these. Furthermore, non-separated organic solids are recycled back to said reactor to undergo further hydrolysis and acidification.

In the current description we refer to the following definitions:

Sewage Sludge:
Solid constituent of sewage rich in organic matter and excess biomass (also referred to as excess sludge) created during the process of wastewater treatment
Main Components:
Total suspended solids (TSS) (mg/l): 5000 to 300000
Organic solids (m/m % of TSS): 50 to 90
pH: 6 to 8
C (m/m % of TSS): 51 to 53
N (m/m % of TSS): 4 to 8
P (m/m % of TSS): 1 to 4
Hydrolysis:
Break down of complex compounds, mainly organic solids (e.g. carbohydrates, protein and lipids) to smaller molecular weight compounds such as sugars, amino acids, fatty acids, etc.
Acidification:
After hydrolysis the conversion of sugars and amino acids into carbon dioxide, hydrogen, ammonia, and organic acids by acidifying bacteria.
Dry Solid or Total Solid (DS):
Solid material comprising digestible organic matter, also known as "Volatile Solids" (VS), and non-biodegradable residues, often referred to as "Fixed Solids" (FS); remains after evaporation of a liquid dried at 105° C. for two hours; measured in mg/l.
Total Dissolved Solid (TDS):
Combined measurement of all organic and inorganic compounds in a liquid after being filtered through a filter having the pore size of 0.45 micrometer, measured in mg/l.
Total Suspended Solid (TSS):
The difference between DS and TDS, measured in mg/l.
Spent solids:
The part of organic solids that cannot be hydrolyzed any further.

Organic Slurry:
An aggregate comprising suspended solids, dissolved solids, compounds containing nitrogen and/or phosphorus, and other macro and micro elements in a liquid.
Volatile Fatty Acids (VFA):
Low molecular weight fatty acids with a carbon chain of six carbons or less (Formic C1; Acetic C2; Propionic C3; Butyric C4; Valeric C5; Caproic C6). VFA are also referred to as short-chain fatty acids (SOFA) or carboxylic acids and result from fermentation or hydrolysis of organic matter.
Valuable Nutrients:
Nutrient elements as identified in EU regulation No 2003/2003, namely:
primary nutrients such as nitrogen in the form of ammonium nitrogen (NH4-N), phosphorus in the form of phosphates (PO4-P), and potassium,
secondary nutrients such as calcium, magnesium, sodium, sulfur and
micro-nutrients such as boron, cobalt, copper, manganese, iron, molybdenum, zinc
Thermophiles:
Bacteria with an optimal growth temperature of 45 to 70 degree Celsius
Thermophilic biological reactor (also referred to as reactor):
An enclosed gas tight reactor with openings and accessories which ensure growth of thermophiles for degradation of organic waste
Micro-aerophilic condition:
A physical condition created to maintain the growth of bacteria that require lower levels of oxygen than that present in the atmosphere to survive; indicated by a redox value measured
Permeate:
Substances like gas, liquid or vapor passed through a purification means while impurities such as insoluble solids are withhold by said means.
COD:
"Chemical oxygen demand" of organic compounds present in a sample of water; determines the amount of organic matter; useful measure of water quality; expressed in mg/l; indicating the mass of oxygen consumed per liter of solution
sCOD:
Soluble (or dissolved) chemical oxygen demand expressed in mg/L
tCOD:
Total chemical oxygen demand of a sample is the amount of oxygen required to completely oxidize organic compounds to carbon dioxide and water; expressed in mg/L
Hydrolysis Efficacy:
Measured as an increase in the sCOD:tCOD ratio.

Biological treatment of organic waste is a well-established field of research and development. In the last few years, research has focused more on trying to recover valuable matter from organic solids, e.g. compost fertilizer, biogas, nitrogen and phosphorus, as part of treating and managing organic solids.

It is known that U.S. Pat. No. 7,927,491 discloses a method and system for integrating an anaerobic bio-digester with a gas cleaner which can recover nutrients while cleaning the biogas produced by the anaerobic bio-digester. However, this solution reclaims valuable components in the biogas generation phase only.

European Patent No EP0053777 discloses a process for hygenizing sewage sludge at thermophilic temperatures and an apparatus thereof. However, the process was not tuned to use the hydrolyzing capabilities of thermophilic bacteria and the disclosed apparatus primarily aimed at disinfection of sludge from pathogenic bacteria where sludge was fed and removed batchwise at a 1:1 ratio.

A disadvantage of the disclosed process and apparatus is that sludge, VFA and valuable nutrients remain mixed when removed from the disclosed apparatus;

thermophiles leave the disclosed apparatus each time a batch of sludge is removed;

VFA accumulated in the disclosed apparatus become toxic to the thermophilic bacteria thus limiting the degree of hydrolysis and acidification.

The present invention represents a further development of the organic waste hydrolysis and acidification technology known from prior art.

The aim of the current invention was to improve efficacy and yield of hydrolysis and acidification of homogenized organic waste in a reactor by removing already during hydrolysis and acidification spent solids and a permeate comprising soluble carbon, VFA and valuable nutrients which may then be further utilized in separate processes.

In the following the invention is presented with reference to FIG. 1, FIG. 2 and the List of references.

One object of the present invention consists in a method of hydrolysis and acidification of homogenized organic waste fed into a b closed and gas tight reactor using natural enzymes released by bacteria under thermophilic conditions where water may be added to said b reactor and the content of the b reactor can be mixed, subjecting during hydrolysis and acidification an adequate part of a suspension formed in the b reactor to i. a separation step isolating
   a permeate comprising an aqueous solution of soluble carbon, volatile fatty acids (VFA) and valuable nutrients,
   an organic slurry comprising an aqueous solution of insoluble organic solids rich in thermophilic bacteria and non-hydrolyzed organic solids, and the remaining part of soluble carbon, VFA and valuable nutrients not being isolated in the permeate,
   thereafter to
ii. a recirculation step re-feeding the organic slurry of step i. into the b reactor for further hydrolysis and acidification and
iii. a release step discharging the permeate of step i. from the b reactor for further use and to
iv. a removal step optionally discharging spent solids contained in the suspension from the reactor,
while
v. optionally adjusting pressure in the b reactor to ensure an equilibrium,
vi. optionally adding air or oxygen to the b reactor to ensure micro-aerophilic conditions,
vii. optionally adjusting pH to a value between 4 to 7,
viii. optionally maintaining temperature between 45 to 70 degree Celsius,
ix. optionally maintaining redox at a value in the range of (−500) mV to +200 mV.

According to the invention homogenized fresh non-hydrolyzed diluted organic slurry is conveyed through a feed pipe to the b reactor, either batchwise (hereinafter discontinuously) or continuously or semi-continuously. The content of the b reactor is continuously agitated inside the b reactor by means of a m mixer. The hydraulic detention time of the slurry in the b reactor ranges from 1 to 24 hours, preferably from 8 to 12 hours. Temperature is optionally adjusted by a 8 means for heating and cooling attached to the b reactor to a value in the range of 45 to 70 degree Celsius, preferably 60 to 65° C. The pH value in the b reactor is maintained between 4 to 7, preferably around 6.0 to 6.8, by addition of acid through a 9 pH adjustment means when the value rises above 6.8 or by addition of alkali through the same 9 means when the pH value drops below 6. The redox potential in the b reactor is maintained at a range of (−500) mV to +200 mV, preferably (−300) mV to (−200) mV.

During this hydrolysis and acidification phase the homogenized organic solids (also referred to as organic slurry) present which have a low to medium concentration of around 2 to 15 m/m %, more particularly 5 to 7 m/m % and a particle size of 0.1 to 10 mm, more particularly 1 to 6 mm are degraded in the b reactor. Hydrolyzed and acidified solids may be further utilized in separate processes, e.g. generation of biogas.

Another object of the present invention consists in an apparatus for carrying out the method described above, comprising at least one b closed and gas tight reactor having openings at least to feed organic waste and to add water, a mixer to stir its content and at least one cycle loop with the following attached elements:

i. at least one 1 separation means to isolate
   a permeate comprising an aqueous solution of soluble carbon, volatile fatty acids (VFA) and valuable nutrients and
   an organic slurry comprising an aqueous solution of insoluble organic solids rich in thermophilic bacteria and non-hydrolyzed organic solids, and the remaining part of soluble carbon, VFA and valuable nutrients not being isolated in the permeate
   and optionally to discharge the permeate from the b reactor,
ii. at least one 2 removal means to take samples of organic solid from the b reactor, measure concentration of fixed solids in said samples and optionally remove spent solids from the b reactor,
iii. at least one 3 aspiration means for adding air or oxygen to the b reactor to ensure micro-aerophilic conditions therein,
iv. at least one 4 pressure adjustment means to regulate headspace pressure in the b reactor, having a withdrawal cycle and a filling cycle,
v. at least one 8 means for heating and cooling to control temperature in the b reactor,
vi. optionally at least one 9 pH adjustment means to regulate the pH value in the b reactor.

The method and apparatus of the present invention are suitable for the hydrolysis and acidification of any organic waste, including wastewater sludge, food processing waste, commercial waste, agricultural waste, organic municipal solid waste, animal manure, industrial by-products like Category 2 and Category 3 waste according to EU regulation no. 1069/2009, or a mixture thereof. The present invention particularly relates to organic waste with high content of carbohydrates, lipids and proteins. The organic waste may be fed continuously, semi-continuously or discontinuously to the b reactor through an a feed pipe.

Hydrolyzed and acidified slurry leaving the b reactor at the bottom is agitated by g, f recirculation pumps mounted into c, h recirculation pipes attached to the b reactor. The g pump forwards the slurry to a 1 separation means mounted into the h pipe. The c recirculation pipe is part of a first cycle loop while the h recirculation pipe might be part of a second or the same cycle loop.

Soluble carbon, VFA and valuable nutrients are isolated in form of a permeate from the slurry by said 1 separation means.

In a preferred embodiment of the invention separating of the permeate from the organic slurry is performed by filtration.

The 1 separation means is composed among others of at least one 6 removal opening to release the permeate, at least one plastic or porous ceramic 5 filter with a pore size of 0.001 to 10 μm, preferably 0.1 μm, and of at least one 7 passage opening for entering and/or circulating the suspension (or organic slurry) from and back to the b reactor. Plastic and ceramic are both materials being resistant to acid and high temperature. The porous ceramic 5 filter may consist of several pipes or flat plates to enlarge the surface separating the permeate and the organic slurry. The 1 separation means might also use as 5 filter a membrane. A j release pipe with a valve is attached the 6 removal opening to adjust release of the liquid permeate. Organic slurry rich in thermophilic bacteria and non-hydrolyzed solids retained after separation is re-fed to the b reactor through the h recirculation pipe attached to the b reactor on one side and to a 7 passage opening of the 1 separation means on the other side.

Components in the organic slurry rejected by the separation as their dimensions are larger than the pore size of the 5 filter, are re-cycled to the b reactor through the h recirculation pipe. This leads in the b reactor to a higher concentration of thermophilic bacteria performing the tasks of hydrolysis and acidification. Recycle of slurry increases the solids retention time and therefore the yield of hydrolysis and acidification.

Discharging the permeate comprising soluble carbon, VFA and valuable nutrients from the b reactor through the j release pipe on a continuous basis prevents the VFA concentration (and subsequent drop in pH values) to reach toxic levels of the hydrolyzing and acidifying bacteria. In fact, the degradation of protein which leads to the release of ammonia aids the biological process by increasing the buffering capacity in the b reactor and stabilizing the reactor pH to remain within the desired range.

Optionally feeding homogenized slurry to the b reactor through the a feed pipe can be a continuous or discontinuous process. In a discontinuous feed process slurry is fed in regular or irregular intervals whereas the discharge of the permeate through the j release pipe may be continuous. In a continuous feed process both feeding the slurry and the withdrawal of the permeate through the j release pipe are continuous. In a preferred embodiment of the invention total amount of homogenized slurry fed either continuously or discontinuously is less than or equal to the amount of discharged permeate, that is discharging the permeate from the hydrolysis and acidification process and feeding additional homogenized organic waste to the b reactor is carried out at a 1:1 ratio. In order to prevent hydraulic imbalance in the b reactor (e.g. reduction of liquid levels) make-up water is optionally added to the b reactor through a k water pipe.

Because the feeding of homogenized slurry to the b reactor and the discharge of the permeate through the j release pipe can have an effect on the liquid level of the b reactor, pressure conditions in the headspace of the b reactor may become instable.

In a preferred embodiment of the invention the method and apparatus are suitable for adjusting the headspace pressure in the b reactor by a 4 pressure adjustment means. The 4 means intakes the gas formed during hydrolysis and acidification and feeds the gas into the b reactor when pressure drops in the b reactor due to removal of the permeate and/or spent solids. The 4 means is mounted to an i adjustment pipe attached to the b reactor. This prevents letting uncontrolled volume of gas pass through the i adjustment pipe into the b reactor. The 4 means is preferably a gas balloon. It might also be an appropriate valve system.

Furthermore, it is preferred that removing spent solids from the hydrolysis and acidification process is performed when the concentration of fixed solids in the hydrolyzed organic slurry reaches a preset value, preferable 40 to 50 m/m % as this concentration indicates the build-up of spent solids in the b reactor. Concentration of fixed solids and spent solids are measured continuously to determine the rate of removal. The 2 removal means comprises a valve mounted to a e removal pipe attached to the b reactor or to a c, h recirculation pipe attached to the b reactor.

To ensure microaerophilic conditions in the b reactor the amount of gas (air or oxygen) injected into the recycled slurry is controlled by an 3 aspiration means. In a preferred embodiment of the invention is the 3 aspiration means composed of a self-aspirating injector with a valve mounted to an d aspiration pipe attached to the b reactor.

An important advantage of the method and apparatus of the invention is that
- already during hydrolysis and acidification spent solids and a permeate comprising soluble carbon, VFA and valuable nutrients can be removed from the organic slurry thus allowing
  - a higher load of the b reactor at lower capital and operating costs compared to reactors used for traditional hydrolysis and acidification,
  - additional processing of the permeate to recover the VFA the value of which is well known,
  - additional processing of the other product, the valuable nutrients which are an excellent source of fertilizer for plant nutrition,
- the recirculation of un-hydrolyzed organic matter rich in thermophilic bacteria to the b reactor after separation speeds up hydrolysis of the organic slurry.

LIST OF DRAWINGS

FIG. 2 is also a block diagram.

| List of reference numbers | |
|---|---|
| Elements referred to | Number |
| Separation means | 1 |
| Removal means | 2 |
| Aspiration means | 3 |
| Pressure adjustment means | 4 |
| Filter | 5 |
| Release opening | 6 |
| Passage opening | 7 |
| Means for heating and cooling | 8 |
| Means for pH adjustment | 9 |
| Feed pipe | a |
| Reactor | b |
| Recirculation pipe | c |
| Aspiration pipe | d |
| Removal pipe | e |

-continued

List of reference numbers

| Elements referred to | Number |
|---|---|
| Recirculation pump | f |
| Recirculation pump | g |
| Recirculation pipe | h |
| Adjustment pipe | i |
| Release pipe | j |
| Water pipe with valve | k |
| Mixer | m |

Arabic numbers refer to claimed elements while elements known to the public are marked with letters.

In the following examples are presented to show some details of the method and means according to the present invention without the intention of limitation.

EXAMPLES

Figure 1:
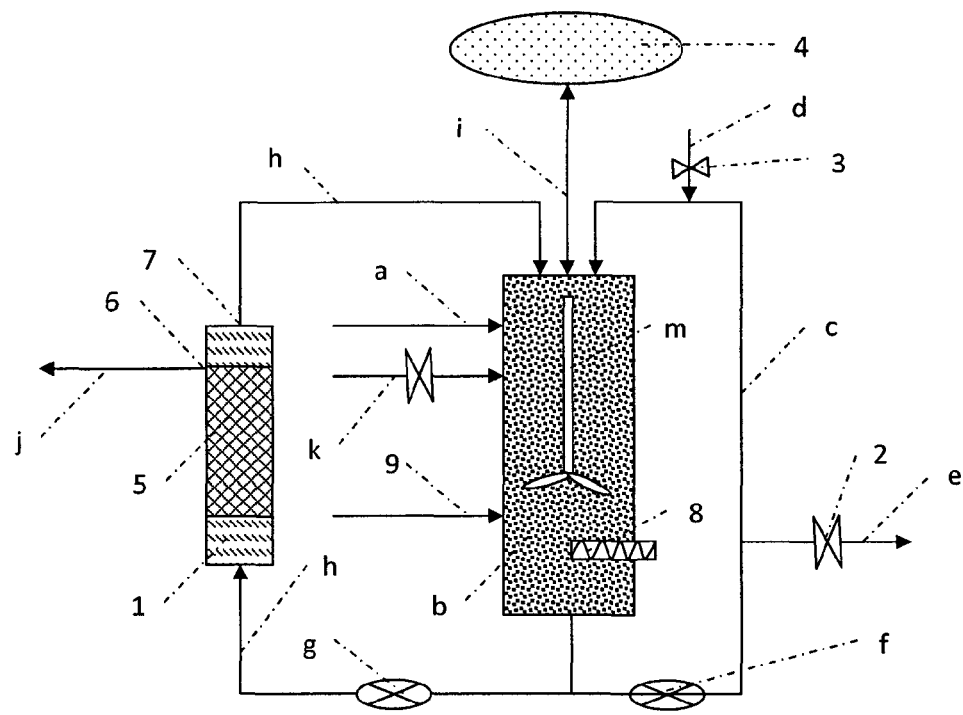
FIG. 1 shows a block diagram of a preferred embodiment according to the invention having two cycle loops, one for the separation of the permeate and one for the removal of spent solids.
Figure 2:
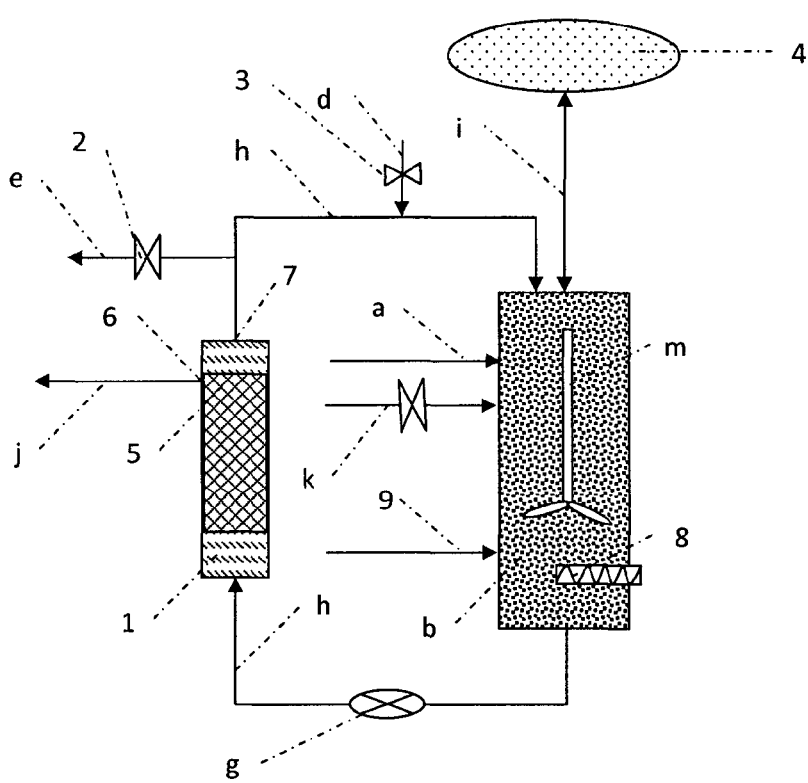
FIG. 2 shows another preferred embodiment according to the invention having one cycle loop only.

The examples below use a b closed and gas tight reactor for biodegradation of organic solids under thermophilic conditions (60 to 65° C.) in less than 24 hours as shown in FIG. 1 or 2, where said b reactor has the following parameters:

capacity: 800 l,
material: stainless steel,
average detention time of the organic slurry: 10 hours and the following elements attached:

m mixer,
8 water jacket,
1 pipe with 5 porous ceramic membrane filter mounted into it, having a pore size of 0.1 μm, a 6 release opening, a j release pipe attached to it and two 7 passage openings,
a feed pipe,
d aspiration pipe with 3 self-aspirating injector having a valve,
k water pipe,
at least one h recirculation pipe,
at least a g recirculation pump,
9 pH adjustment pipe
e removal pipe with a 2 valve and
4 gas balloon attached to an i adjustment pipe.

Example 1—Method for Hydrolyzing and Acidifying Organic Waste Cyclically Fed into a Reactor and an Apparatus Thereof Waste activated sludge from a municipal wastewater plant received at a dry solids concentration of around 15 m/m % is pre-treated (homogenized) first by diluting it using tap water to a concentration of around 5 m/m % dry solids and then using a grinder with a 1 mm sieve to bring the particle size of the solids down to 1 mm.

After pre-treatment the homogenized fresh non-hydrolyzed water-diluted organic slurry is fed to the b reactor cyclically every two hours through the a feed pipe. The slurry remains for 8 to 12 hours in the b reactor. When the concentration of fixed solids in the b reactor is higher than 40 m/m %, spent solids are removed from the b reactor using the 2 valve attached to the e removal pipe. The remaining sludge is recycled to the b reactor through the c recirculation pipe of a first cycle loop.

Hydrolyzed and acidified sludge leaving the b reactor through the h recirculation pipe of a second cycle loop is agitated by the g recirculation pump and is pressed through the 5 membrane filter attached to the h recirculation pipe.

Soluble carbon, VFA and valuable nutrients are discharged from the 5 filter continuously in form of a permeate through the 6 opening of the 1 pipe mounted to the h recirculation pipe of the left cycle loop.

Slurry unable to pass through the 5 filter is recycled back to the b reactor through the h recirculation pipe attached to the 7 passage opening of the 1 pipe.

Pressure variation inside the b reactor is maintained to a relatively constant level using the 4 gas balloon. During the course of hydrolysis and acidification the evaporating gases, vapors are collected in the 4 balloon. When the pressure drops in the b reactor the content of the 4 balloon helps to keep the headspace pressure in the b reactor constant.

Temperature of 60 to 65° C. is maintained using the 8 water jacket mounted on the external wall of the b reactor.

pH inside the b reactor is initially set to a value of 6.5 by adding acid through the 9 pH adjustment pipe and kept in the range of 6.0 to 6.8 without adding chemicals.

Microaerophilic regime inside the b reactor is maintained using the 3 self-aspirating injector mounted onto the d aspiration pipe to maintain a redox value of around (−250) mV inside the b reactor.

Table 1 enlists the parameters of samples of sludge slurry (before entering the b reactor) taken on three different days:

TABLE 1

Samples of slurry before fed to the reactor

| | COD (kg/day) | DS (%) | tCOD (g/kg) | sCOD (mg/l) | VFA (mg/l acetate) | NH4—N (mg/l) |
|---|---|---|---|---|---|---|
| Sample 1 | 50-60 | 3.90 | 43.0 | 2800 | 656 | 465 |
| Sample 2 | | 6.52 | 71.7 | 3800 | 226 | 216 |
| Sample 3 | | 5.62 | 61.8 | 3200 | 100 | 150 |

Table 2 shows the results achieved concerning the permeate corresponding to the slurry samples of Table 1 fed into the b reactor:

TABLE 2

Permeate characteristics

| | VFA (mg/l) | sCOD (mg/l) | NH4—N (mg/l) |
|---|---|---|---|
| Sample 1 | 2339 | 6000 | 900 |
| Sample 2 | 2387 | 10000 | 1420 |
| Sample 3 | 3239 | 12600 | 1340 |

Checking the data of the permeate the results show clearly that the process significantly improves the hydrolysis and acidification of the organic solids. Table 2 shows a 3.5 to 30 fold increase in performance measured in terms of the VFA present, soluble carbon present and valuable nutrients comprised in the permeate.

Example 2

A variation of the method and apparatus described in Example 1 is presented in FIG. 2 where the b reactor has only one cycle loop.

The invention claimed is:
1. A method for obtaining a permeate in aqueous solution from a homogenized organic waste wherein the obtained permeate comprises low molecular weight fatty acids with a C1-C6 carbon chain and
valuable nutrients selected from the group consisting of: nitrogen in the form of ammonium (NH4-N) or nitrate (NO3-N), phosphorus in the form of phosphates (PO4-P), potassium, calcium, magnesium, sodium, sulfur, boron, cobalt, copper, manganese, iron, molybdenum and zinc, comprising the steps of:
i. feeding the homogenized organic waste into a closed and gas tight, mixed reactor,
ii. hydrolyzing and acidifying the waste in the reactor under thermophilic and microaerophilic conditions utilizing natural enzymes released by bacteria present in the waste,
iii. separating the hydrolyzed and acidified waste obtained in step ii into
the permeate; and
an organic slurry rich in thermophilic bacteria,
iv. re-feeding the organic slurry and a suspension formed in the reactor into the reactor for further hydrolysis and acidification,
v. discharging the permeate from the reactor for further use,
vi. discharging spent solids contained in the suspension from the reactor when the concentration of fixed solids in the suspension reaches a value of 40 to 50 m/m %,
vii. measuring temperature, redox potential, pH, and fixed solid concentration in the reactor,
viii. adjusting head space pressure in the reactor to a constant equilibrium by feeding gas, formed during hydrolysis and collected in a pressure adjustment means, from said pressure adjustment means into the reactor when pressure drops in the reactor due to removal of the permeate and/or spent solids from the reactor,
ix. adjusting the pH in the reactor to a value between 6.0 to 6.8 by addition of acid when the pH value rises above 6.8 or by addition of alkali when the pH value drops below 6.0,
x. maintaining the temperature in the reactor between 60 to 65 degree Celsius by a means for cooling and heating to ensure thermophilic conditions therein,
xi. maintaining microaerophilic conditions in the reactor by adjusting the redox potential in the range of (−300) mV to (−200) mV by adding air or oxygen thereto,
xii. adding water to the reactor separately when releasing the permeate to ensure a 1:1 ratio of the homogenized organic waste fed into the reactor, and the permeate and/or the spent solids released thereof, and
xiii. ensuring a hydraulic detention time of the waste of up to 24 hours.

2. The method according to claim 1, wherein the organic waste is obtained from the group selected from wastewater sludge, food processing waste, commercial waste, agricultural waste, organic municipal solid waste, animal manure, industrial by-products selected from the group of condemned meat, manure and gut contents, catering waste from households or restaurants, former food, waste blood or feathers, or a mixture thereof, organic waste with a high content of carbohydrates, lipids and proteins.

3. The method according to claim 1, comprising the step of separating the permeate from the hydrolyzed and acidified waste by filtration.

4. The method according to claim 1, wherein the pressure adjustment means is a gas balloon.

5. The method according to claim 1, carrying out the feeding of the homogenized organic waste and/or the adding of the water continuously, semi-continuously or discontinuously at a 1:1 ratio.

* * * * *